US006760098B2

(12) United States Patent
Salo

(10) Patent No.: US 6,760,098 B2
(45) Date of Patent: Jul. 6, 2004

(54) REFRACTOMETER

(75) Inventor: Harri Salo, Vantaa (FI)

(73) Assignee: Janesko Oy, Vantaa (FI)

( * ) Notice: Subject to any disclaimer, the term of this patent is extended or adjusted under 35 U.S.C. 154(b) by 193 days.

(21) Appl. No.: 09/918,528

(22) Filed: Aug. 1, 2001

(65) Prior Publication Data

US 2002/0018200 A1 Feb. 14, 2002

(30) Foreign Application Priority Data

Aug. 1, 2000 (FI) .............................................. 20001733

(51) Int. Cl.$^7$ .............................................. G01N 21/41
(52) U.S. Cl. ........................ 356/135; 356/136; 356/128
(58) Field of Search ................................. 356/136, 135, 356/128, 157, 481, 504, 517, 134

(56) References Cited

U.S. PATENT DOCUMENTS

| | | | |
|---|---|---|---|
| 4,451,147 A | | 5/1984 | Dobes et al. |
| 5,585,729 A | | 12/1996 | Toshima et al. |
| 6,067,151 A | * | 5/2000 | Salo ........................... 356/136 |
| 6,130,439 A | * | 10/2000 | Le Menn ..................... 250/573 |
| 6,457,478 B1 | * | 10/2002 | Danese ....................... 134/1.3 |
| 6,500,699 B1 | * | 12/2002 | Birdsley et al. ............ 438/121 |
| 6,506,949 B2 | * | 1/2003 | Gillis et al. ................. 568/939 |

FOREIGN PATENT DOCUMENTS

| | | |
|---|---|---|
| DE | 42 14 572 | 11/1993 |
| DE | 44 18 180 | 1/1996 |
| EP | 0 836 092 | 4/1998 |
| FI | 93583 | 1/1995 |
| FI | 980221 | 7/1999 |

OTHER PUBLICATIONS

Teflon PTFE 8 fluoropolymer resin Product Information, 6/99, Du Pont.*

* cited by examiner

Primary Examiner—Russell Adams
Assistant Examiner—Andrew Sever
(74) Attorney, Agent, or Firm—Burns, Doane, Swecker & Mathis, L.L.P.

(57) ABSTRACT

The invention relates to a refractometer comprising an optical module (4) arranged floatingly inside a housing structure, which module comprises an optical window (2) to be positioned in a process fluid (3), and means for forming an illuminating beam and for directing it into the process fluid (3) through the optical window (2) and for directing back the part of the illuminating beam that is reflected from the process fluid, and further, means for watching the image formed in said manner. The optical module (4) is arranged to be supported against the housing structure by means of sealing (5) arranged between the optical window (2) and the housing structure. In order to provide a device suitable for difficult conditions, the housing structure part (6) in contact with the process fluid (3) against which the optical window (2) is arranged to be supported via sealing (5) is formed of a material that is chemically durable, mechanically rigid and durable and has good thermal conductivity.

20 Claims, 1 Drawing Sheet

REFRACTOMETER

The present application claims priority pursuant to 35 U.S.C. §119 from Finnish Patent Application No. 20001733, the entire contents of which is incorporated by reference herein.

BACKGROUND

1. Field of the Invention

The invention relates to a refractometer and, more particularly, to a refractometer comprising an optical module arranged floatingly inside a housing structure for measuring the index of refraction of a process fluid.

2. Background Information

The operational principle of a refractometer has been known for over a hundred years. Today, refractometers are rather widely used on several different fields. The range of use of refractometers include food processing industry, wood processing industry, chemical industry and different researches in general.

The operational principle of a refractometer can be described by way of principle in the following manner. A refractometer measures the refractive index of the process fluid by means of total reflection generated at the interface between the optical window and the fluid. The illuminating beam from the source of light is directed at the interface between the optical window and the process fluid. Part of the illuminating beam is totally reflected from the fluid, whereas part of it is partly absorbed into the fluid. This results in an image in which the location of the light and dark areas depends totally on the critical angle of the total reflection, and thus on the refractive index of the process fluid.

The essential aspect of refractometer measuring is the analysis of the image generated by the reflection of light. The objective of said image analysis is to find the critical angle of the total reflection, in other words the interface at which the light area of the image formed in the above-described manner changes over to a dark area.

As becomes obvious from the above-described aspects, the operation of a refractometer is based on very accurate angle measurement, because the critical angle of the total reflection is determined according to the refractive index of two materials. The problem with older refractometers has been angle variations of the optical window relative to the housing structure of the device. The angle variations are frequently due to the fact that the optical window in these devices is attached by means of a flexible sealing material. If the optical window is rigidly attached to the housing structure, the sealing material has to be very elastic, and thus certain materials with weak elasticity cannot be used. In several known refractometers, the optics and the light detector are rigidly attached to the housing, so that another problem is caused by an error in the angle measurement caused by the distortion of the housing structure.

To eliminate said drawbacks, a refractometer of a novel type has been provided, being disclosed in U.S. Pat. No. 6,067,151. The advantage of this solution is that the optical window can be attached also by using a weakly elastic seal, such as Teflon, without the accuracy of the angle measurement suffering from this at all.

The refractometer described in U.S. Pat. No. 6,067,151 functions extremely well in certain environments, but a problem is caused by measurement of aggressive fluids, for instance. Aggressive fluids include strong acids and basses, such as hydrochloric acid (HCl), hydrofluoric acid (HF), nitric acid (HNO3) and sulfuric acid (H2SO4), as well as sodium (NaOH) and potassium (KOH) hydroxides and ammonia (NH4OH). A plurality of acids and bases strongly corrode most of the structural metals, and alternative metals are expensive and difficult to be machined (such as tantalum and zirconium). Further, problems are caused in measurement of less aggressive fluids in cases where impurities and metal ions are not desirable in the process fluid. In such cases, the process surfaces of tube systems and instruments must not contain any metal part.

SUMMARY

An object of the invention is to provide a refractometer by means of which the drawbacks of the prior art can be eliminated. This has been achieved by means of a refractometer according to the invention. The refractometer according to the invention comprises an optical module arranged floatingly inside a housing structure, which module comprises an optical window to be positioned in a process fluid, and means for forming an illuminating beam and for directing it into the process fluid through the optical window and for directing back the part of the illuminating beam that is reflected from the process fluid, and further, means for watching the image formed in said manner, whereby the optical module is arranged to be supported against the housing structure by means of sealing arranged between the optical window and the housing structure. The housing structure part in contact with the process fluid against which the optical window is arranged to be supported via sealing is formed of a material that is chemically durable, mechanically rigid and durable and has good thermal conductivity.

An advantage of the invention is, above all, the applicability of the structure to the measurement of very different fluids. The solution is also simple, which enables the use of plastic materials, for example, in such parts that are not in contact with the process fluid or are not mechanically subjected to great stress, so that the manufacturing costs remain low.

BRIEF DESCRIPTION OF THE FIGURES

The invention will now be described in greater detail by means of a preferred application example illustrated in the attached drawing, whereby.

DETAILED DESCRIPTION

Figure 1:
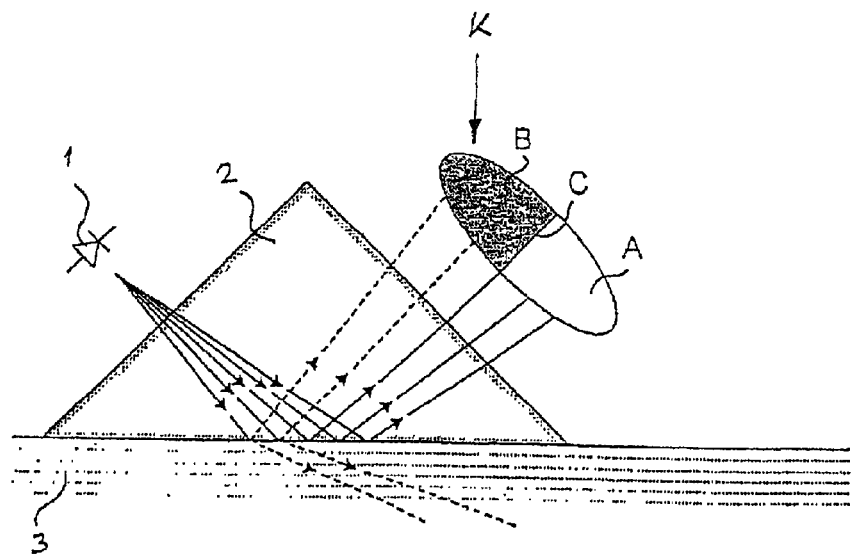
FIG. 1 shows a principled diagrammatic view of the operation principle of a refractometer.

FIG. 1 shows a principled diagrammatic view of the operation principle of a refractometer. In FIG. 1, reference numeral 1 denotes a source of light and reference numeral 2 denotes an optical window, which can be a prism, for example. Reference numeral 3 indicates a process fluid.

As mentioned above, a refractometer measures the refractive index of the process fluid by means of total reflection generated at the interface between the optical window 2 and the process fluid 3. The operation principle of a refractometer represents the prior art obvious to those skilled in the art, so that aspects related thereto are not described in more detail herein. In this connection, only the essential basic principle is explained.

An illuminating beam from the source of light 1 is directed at the interface between the optical window 2 and the process fluid. The illuminating beam is shown in FIG. 1 in a principled manner by means of arrows. Part of the illuminating beam is totally reflected back from the process fluid 3, whereas part of it is partly absorbed into the fluid. This results in an image K, in which the location of the interface C between the light area A and the dark area B depends on the critical angle of the total reflection, and thus on the reflective index of the process fluid.

The operation of the refractometer is thus based on extremely accurate angle measurement, because the critical angle of the total reflection is determined according to reflective indices of two materials. As mentioned earlier, the problem with several refractometers known from the prior art has frequently been angle variations of the optical window relative to the housing of the device, because the optical window is in several solutions attached to the housing by means of a flexible sealing material. The use of a flexible material as sealing has been due to the fact that if the optical window is rigidly attached to the housing, the sealing material has to be very elastic, and thus materials with weak elasticity cannot be used. In several known refractometers the optics and the light detector are rigidly attached to the housing, so that another problem has been caused by an error in the angle measurement due to the distortion of the housing.

Figure 2:
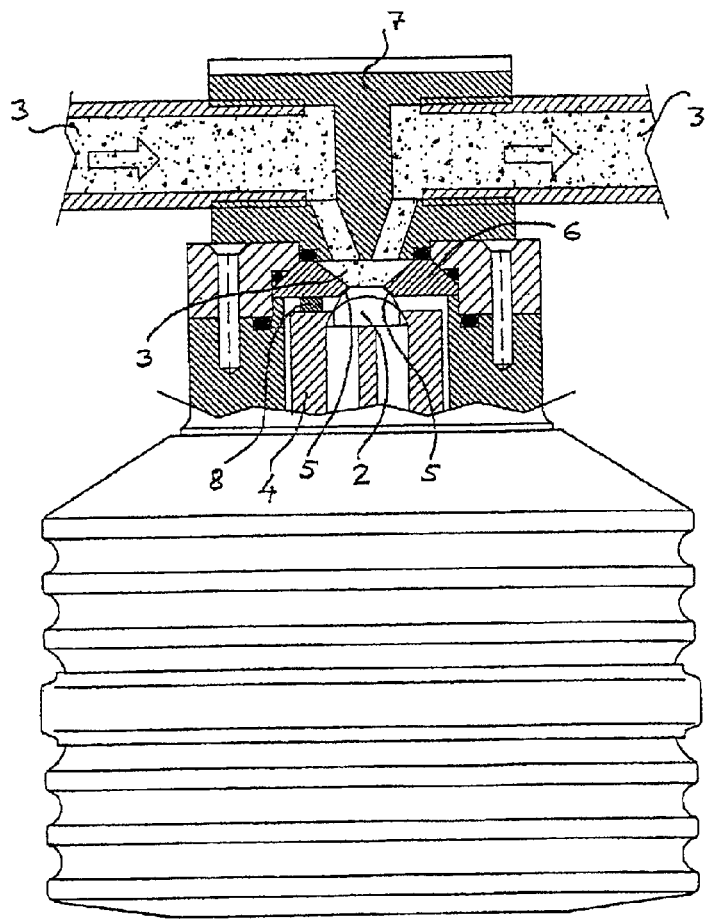
FIG. 2 shows a principled side view of a refractometer according to the invention.

In order to eliminate the above drawbacks, a solution has been provided in which a source of light 1, an optical window 2, means for directing he illuminating beam, and the light detector are arranged in a rigid optical module 4, which is shown in FIG. 2. The optical module 4 is floatingly arranged to be supported by sealing 5 arranged between the housing structure and the optical window. The sealing can be cone sealing, for example, or it can form a spherical surface, etc. Since the optical module 4 floats supported by the sealing 5 relative to the housing structure or other mechanics of the device, external forces, such as forces generated by the flow of the process fluid, mechanical stress in the tube system, heat expansion and pressure, do not affect the accuracy of the measurement. Owing to the floating optical module 4, also materials with weak elasticity, such as a polytetrafluoroethylene material, e.g.—Teflon, can be used in the sealing of the optical window, for instance a prism.

The optical module 4 is pressed against the sealing by means of appropriate spring members, whereby the compressive force is constant in all temperatures. Thus, the spring members together with the floating optical module compensate for the weak elasticity of certain sealing materials. The spring members are mounted in such a way that no process heat is conducted into the optical module through them. The spring members are not shown in FIG. 2, but U.S. Pat. No. 6,067,151 which is incorporated by reference herein, the structure being described in more detail in said application.

The floating optical module 4 is in contact with the process fluid 3 and the tip 6 of the housing structure, i.e. the part of the housing structure that is in contact with the process, only through the optical window 2. The connector surface to the process and the tip of the housing structure is minimized to make thermal conduction more difficult. Between the optical window 2 and the tip 6 of the housing, there is sealing 5. The connector surface must allow small angle changes between the axis of the optical module and the axes of the tip. As mentioned above, the connector surface can be conical, for instance. Owing to the floating optical module, it is also easy to manufacture and maintain the device. The module can be tested as early as before the actual connection to the rest of the technique.

As mentioned above, the optical module 4 includes all optical elements. The optical module also includes a temperature sensor 8, because accurate concentration measurement also requires quick and accurate temperature measurement of the process fluid. The temperature sensor 8 is positioned in the vicinity of the tip of the housing in such a way that the heat contact in the direction of the tip and further to the process fluid is maximized. As regards the positioning of the temperature sensor 8, U.S. Pat. No. 6,067,151 describes this aspect in more detail in said patent. The process fluid 3 is conducted to the optical window by means of a flow vessel 7.

A thin (e.g. 0.25 mm) polytetrafluoroethylene or Teflon film is placed between the cone surface of the optical window 2 at the tip of the optical module and the tip 6 of the housing structure functions as sealing 5, as observed earlier. Due to the weak elasticity of polytetrafluoroethylene (Teflon), the sealing force is produced by means of spring members, as mentioned above. The spring members press the optical module against the cone surface, whereby the conical sealing surface is subjected to the whole sealing force generated by the spring members, for instance approximately 500 Newtons. Said aspect imposes high mechanical requirements on the material of the tip 6 of the housing structure.

The sealing material can be elastic, in which case the sealing force is generated by the material itself, and no external sealing force is required. The geometry of the sealing can also be different, such as an O-ring. In any case, the sealing surface is subjected to great force irrespective of the sealing material or the geometry of the sealing, so that the material used has to be mechanically rigid.

The positioning of the above-mentioned temperature sensor further imposes great additional requirements for the material of the tip 6 of the housing structure. The material must have as good thermal conductivity as possible, and still, it must be durable, since the temperature sensor cannot be in contact with the process fluid for chemical reasons, but the thermal conductivity characteristics must be good in any case. The tip part 6 of the housing structure, i.e. the part in contact with the process fluid 3 of the housing structure, against which the optical window 2 is arranged to be supported via the sealing 5, is formed of a material that is chemically durable, mechanically rigid and durable and has good thermal conductivity. The material can be a ceramic material, for instance. The use of sapphire has turned out to be particularly advantageous, as the manufacturing material of the abovementioned part, since sapphire meets all the above requirements extremely well.

The tip part 6 of the housing structure in the example of FIG. 1 is made of a sapphire disk having a conical sealing surface. The sapphire disk is further attached to other parts of the housing structure, which parts can also be metallic, since they are not in contact with the process fluid 3. It is to be noted that in practice, it is advantageous for different parts of the housing structure to be at least partly made of non-metallic material, for instance Teflon, also outside the process surface, since the process seal can leak. On the process side, the following materials can preferably be used. The tip part of the housing structure can be made of sapphire, and a spinel prism can be used as the prism. A polytetrafluoroethylene (Teflon) film can be used as a prism seal and a pre-fluoroelastomer as O-ring seals. The flow vessel can be made of a fluoro plastic material, for example.

Further, it is to be noted in relation to the invention that the tip part 6 of the housing structure, i.e. the sapphire disk, also functions, in a way, as a member decreasing the pressure stress, since a great sealing force directed at a small surface, i.e. the sealing 5, is directed at a greater surface by means of the rigid sapphire disk, whereby the counter-surface of said surface can be formed in a part made of less rigid material, such as a plastic material.

The above-described application example is by no means intended to restrict the invention, but the invention can be varied totally freely within the scope of the claims. Thus, it is obvious that the refractometer according to the invention and the details thereof do not have to be exactly like the ones shown in the figure, but other solutions are also feasible.

What is claimed is:

1. A refractometer comprising:
   an optical module arranged floatingly inside a housing structure, the optical module comprising
      an optical window to be positioned in a process fluid,
      beam forming and directing means for forming an illuminating beam and for directing the illuminating beam into the process fluid through the optical window and for directing a reflected part of the illuminating beam reflected from the process fluid away from the process fluid, and
      detecting means for detecting an image generated by said beam forming and directing means; and
   a housing structure part arranged to support the optical module inside the housing structure via sealing means for sealing the optical module against the housing structure part, the sealing means being arranged between the optical window and the housing structure part,
   wherein the housing structure part is configured to contact the process fluid and is configured to support the optical window via the sealing means, the housing structure part being formed of a ceramic material.

2. A refractometer comprising:
   an optical module arranged floatingly inside a housing structure, the optical module comprising
      an optical window to be positioned in a process fluid,
      beam forming and directing means for forming an illuminating beam and for directing the illuminating beam into the process fluid through the optical window and for directing a reflected part of the illuminating beam reflected from the process fluid away from the process fluid, and
      detecting means for detecting an image generated by said beam forming and directing means: and
   a housing structure part arranged to support the optical module inside the housing structure via sealing means for sealing the optical module against the housing structure part, the sealing means being arranged between the optical window and the housing structure part,
   wherein the housing structure part is configured to contact the process fluid and is configured to support the optical window via the sealing means, the housing structure part being formed of sapphire.

3. A refractometer according to claim 2, wherein the housing structure part is configured to direct a seating force between the optical window and the housing structure part at a greater surface.

4. A refractometer comprising:
   an optical module arranged inside a housing structure, the optical module comprising
      an optical window to be positioned in a process fluid,
      beam forming and directing means for forming an illuminating beam and for directing the illuminating beam into the process fluid through the optical window and for directing a reflected part of the illuminating beam reflected from the process fluid away from the process fluid, and
      detecting means for detecting an image generated by said beam forming and directing means;
   a housing structure part arranged to support the optical module inside the housing structure; and
   sealing means for sealing the optical module against the housing structure part, the sealing means being arranged between the optical window and the housing structure part,
   wherein the optical module is compressively supported against the housing structure part in a floating manner at an interface between the optical window and the housing structure part, and
   wherein the housing structure part is configured to contact the process fluid, the housing structure part being formed of a ceramic material.

5. A refractometer according to claim 4, wherein said ceramic material is resistant to corrosion by at least one of hydrochloric acid, hydrofluoric acid, nitric acid and sulfuric acid.

6. A refractometer according to claim 5, wherein said ceramic material is resistant to corrosion by hydrochloric acid, hydrofluoric acid, nitric acid and sulfuric acid.

7. A refractometer according to claim 6, wherein said ceramic material is resistant to corrosion by sodium hydroxide, potassium hydroxide and ammonia.

8. A refractometer according to claim 4, wherein said ceramic material is resistant to corrosion by at least one of sodium hydroxide, potassium hydroxide and ammonia.

9. A refractometer according to claim 8, wherein said ceramic material is resistant to corrosion by sodium hydroxide, potassium hydroxide and ammonia.

10. A refractometer according to claim 4, wherein the housing structure part is configured with a conically shaped surface at the interface between the optical window and the housing structure part.

11. A refractometer according to claim 10, wherein the housing structure part is configured to withstand a compressive force of approximately 500 Newtons applied against the conically shaped surface.

12. A refractometer according to claim 4, wherein the housing structure part is configured with a spherically shaped surface at the interface between the optical window and the housing structure part.

13. A refractometer according to claim 12, wherein the housing structure part is configured to withstand a compressive force of approximately 500 Newtons applied against the spherically shaped surface.

14. A refractometer according to claim 14, further comprising a temperature sensor disposed against the housing structure part and adjacent to the optical window such that the temperature sensor is isolated from the process fluid.

15. A refractometer according to claim 14, wherein the ceramic material has a thermal conductivity sufficiently high to allow the temperature sensor to accurately measure a temperature of the process fluid near the optical window via heat conduction through the housing structure part.

16. A refractometer comprising:
    an optical module arranged adjacent to a housing structure, the optical module comprising
       an optical window configured to be positioned in a process fluid,
       a light source configured to emit an illuminating beam, the illuminating beam being directed through the optical window toward an interface between the optical window and the process fluid, a reflected part of the illuminating beam being reflected from said interface and being directed through the optical window away from said interface, and a light detector configured to detect an image comprising light from the reflected part of the illuminating beam;

a housing structure part arranged to support the optical module adjacent to the housing structure; and a seal disposed between the optical window and the housing structure part, wherein the optical module is compressively supported against the housing structure part in a floating manner at an interface between the optical window and the housing structure part, and wherein the housing structure part is configured to contact the process fluid, the housing structure part being formed of sapphire.

17. A refractometer according to claim 16, wherein the housing structure part is configured with a conically shaped surface at the interface between the optical window and the housing structure part.

18. A refractometer according to claim 17, wherein the housing structure part is configured to withstand a compressive force of approximately 500 Newtons applied against the conically shaped surface.

19. A refractometer according to claim 16, wherein the housing structure part is configured with a spherically shaped surface at the interface between the optical window and the housing structure part.

20. A refractometer according to claim 19, wherein the housing structure part is configured to withstand a compressive force of approximately 500 Newtons applied against the spherically shaped surface.

* * * * *